(12) United States Patent
Wright

(10) Patent No.: US 11,213,416 B1
(45) Date of Patent: Jan. 4, 2022

(54) APPENDAGE BRACE ASSEMBLY

(71) Applicant: Nathaniel M. Wright, Haiku-Pauwela, HI (US)

(72) Inventor: Nathaniel M. Wright, Haiku-Pauwela, HI (US)

( * ) Notice: Subject to any disclaimer, the term of this patent is extended or adjusted under 35 U.S.C. 154(b) by 250 days.

(21) Appl. No.: 16/199,137

(22) Filed: Nov. 24, 2018

(51) Int. Cl.
*A61F 5/01* (2006.01)
*A61F 5/32* (2006.01)
*A61F 5/058* (2006.01)

(52) U.S. Cl.
CPC .......... *A61F 5/0118* (2013.01); *A61F 5/0106* (2013.01); *A61F 5/0585* (2013.01); *A61F 5/05858* (2013.01); *A61F 5/32* (2013.01)

(58) Field of Classification Search
CPC ... A61H 2003/007; A61F 5/0127; A61F 5/32; Y10T 24/3913
USPC ............................................................ 602/6
See application file for complete search history.

(56) References Cited

U.S. PATENT DOCUMENTS

| | | | | |
|---|---|---|---|---|
| 3,513,842 A | * | 5/1970 | Berg | A61F 13/00 602/60 |
| 5,466,215 A | * | 11/1995 | Lair | A61F 5/01 602/21 |
| 5,713,836 A | * | 2/1998 | O'keefe | A61F 5/058 602/5 |
| 2006/0036204 A1 | * | 2/2006 | Corrales | A61F 5/00 602/27 |
| 2009/0083947 A1 | * | 4/2009 | Kubli | F16G 11/00 24/115 H |
| 2012/0215146 A1 | * | 8/2012 | Dao | A61F 5/00 602/20 |
| 2014/0052039 A1 | * | 2/2014 | Summit | A61F 5/01 602/21 |
| 2015/0320581 A1 | * | 11/2015 | Causse | A61F 5/01 602/28 |

* cited by examiner

*Primary Examiner* — Rachael E Bredefeld
*Assistant Examiner* — Trisha Talapatra
(74) *Attorney, Agent, or Firm* — Michael W. Goltry; Robert A. Parsons; Parsons & Goltry, PLLC

(57) ABSTRACT

An appendage brace assembly includes an openwork including an open proximal extremity, a distal extremity, and a volume therebetween. The openwork is stiff and jointless, and defines access points to the volume from proximate to the open proximal extremity to proximate to the distal extremity for enabling access to the appendage applied to the volume through the open proximal extremity. A restraint is carried by the openwork for restraining the appendage from being withdrawn from the volume through the open proximal extremity, when the restraint is releasably secured to the appendage applied to the volume through the open proximal extremity, and for enabling the appendage for being withdrawn from the volume through the open proximal extremity without interference from the openwork, when the restraint is released from the appendage applied to the volume through the open proximal extremity.

6 Claims, 10 Drawing Sheets

APPENDAGE BRACE ASSEMBLY

FIELD OF THE INVENTION

The present invention relates to braces for bracing appendages in need of bracing for safety, treatment, or therapeutic purposes.

BACKGROUND OF THE INVENTION

Bracing an appendage in need of bracing, such as arm, a leg, or a part thereof, is routinely needed to enable the appendage to heal, restrict movement of the appendage to alleviate pain or injury, support the appendage to enable the subject to safely engage in physical activity, such as when the appendage is injured, weak, or otherwise prone to injury, etc. Given this ongoing need, skilled artisans have developed an array of braces specifically designed to brace appendages, such as arms and legs, and portions of appendages, such as forearms, elbows, wrists, knees, and ankles. While existing braces are generally suitable and generally work well, they are notoriously expensive, difficult to construct, structurally complex, difficult to use, and not configured to temporarily secure and brace an appendage without impairing direct access to the appendage for therapeutic or treatment purposes.

SUMMARY OF THE INVENTION

According to the principle of the invention, a brace assembly for releasably securing and bracing an appendage in need of bracing, such as an arm of a subject, includes an openwork including an open proximal extremity, a distal extremity, and a volume between the open proximal extremity and the distal extremity. The openwork is stiff, being rigid and not easily bent, and inarticulate, having no articulation or joint and thereby being jointless, and defines access points to the volume from proximate to the open proximal extremity to proximate to the distal extremity for enabling access to the appendage applied to the volume through the open proximal extremity. A restraint is carried by the openwork for restraining the appendage from being withdrawn from the volume through the open proximal extremity, when the restraint is releasably secured to the appendage applied to the volume through the open proximal extremity, and for enabling the appendage for being withdrawn from the volume through the open proximal extremity without interference from the openwork, when the restraint is released from the appendage applied to the volume through the open proximal extremity. The restraint is a noose. The noose is proximate to the distal extremity. The noose is adjustable between a loosened appendage-receiving/releasing position and a comparatively constricted appendage-securing position. The noose includes a loop portion of a line and a sliding coupling closing the loop portion. Further included is a lock for releasably securing the line relative to the openwork for securing the loop portion. The lock is carried by the openwork, and the line extends from the loop portion through the sliding coupling and to the lock. The line extends through the openwork from the sliding coupling to the lock. The line between the sliding coupling and the lock is enclosed within the openwork. The lock is proximate to the open proximal extremity.

According to the principle of the invention, a brace assembly for releasably securing and bracing an appendage in need of bracing, such as an arm of a subject, includes a helical openwork, and a restraint. The helical openwork extends longitudinally from a proximal coil defining a proximal opening to a distal coil defining a distal opening, defines a volume from the proximal opening to the distal opening, is stiff, being rigid and not easily bent, and inarticulate, having no articulation or joint and thereby being jointless, and defines a helical space from the proximal coil to the distal coil defining access points to the volume between the proximal coil and the distal coil for enabling access to an appendage between the proximal coil and the distal coil when the appendage is applied to the volume through the proximal opening. The restraint is carried by the helical openwork for restraining the appendage from being withdrawn from the volume through the proximal opening, when the restraint is releasably secured to the appendage applied to the volume through the proximal opening, and for enabling the appendage for being withdrawn from the volume through the proximal opening without interference from the helical openwork, when the restraint is released from the appendage applied to the volume through the proximal opening. The restraint is a noose. The noose is proximate to the distal coil proximate to the distal opening. The noose is adjustable between a loosened appendage-receiving/releasing position and a comparatively constricted appendage-securing position. The noose includes a loop portion of a line and a sliding coupling closing the loop portion. Further included is a lock for releasably securing the line relative to the helical openwork for securing the loop portion. The lock is carried by the helical openwork, and the line extends from the loop portion through the sliding coupling and to the lock. The line extends through the helical openwork from the sliding coupling to the lock. The line between the sliding coupling and the lock is enclosed within the helical openwork. The lock is secured to the proximal coil.

Consistent with the foregoing summary of illustrative embodiments, and the ensuing detailed description, which are to be taken together, the invention also contemplates associated apparatus and method embodiments.

BRIEF DESCRIPTION OF THE DRAWINGS

Referring to the drawings.

DETAILED DESCRIPTION

Figure 1:
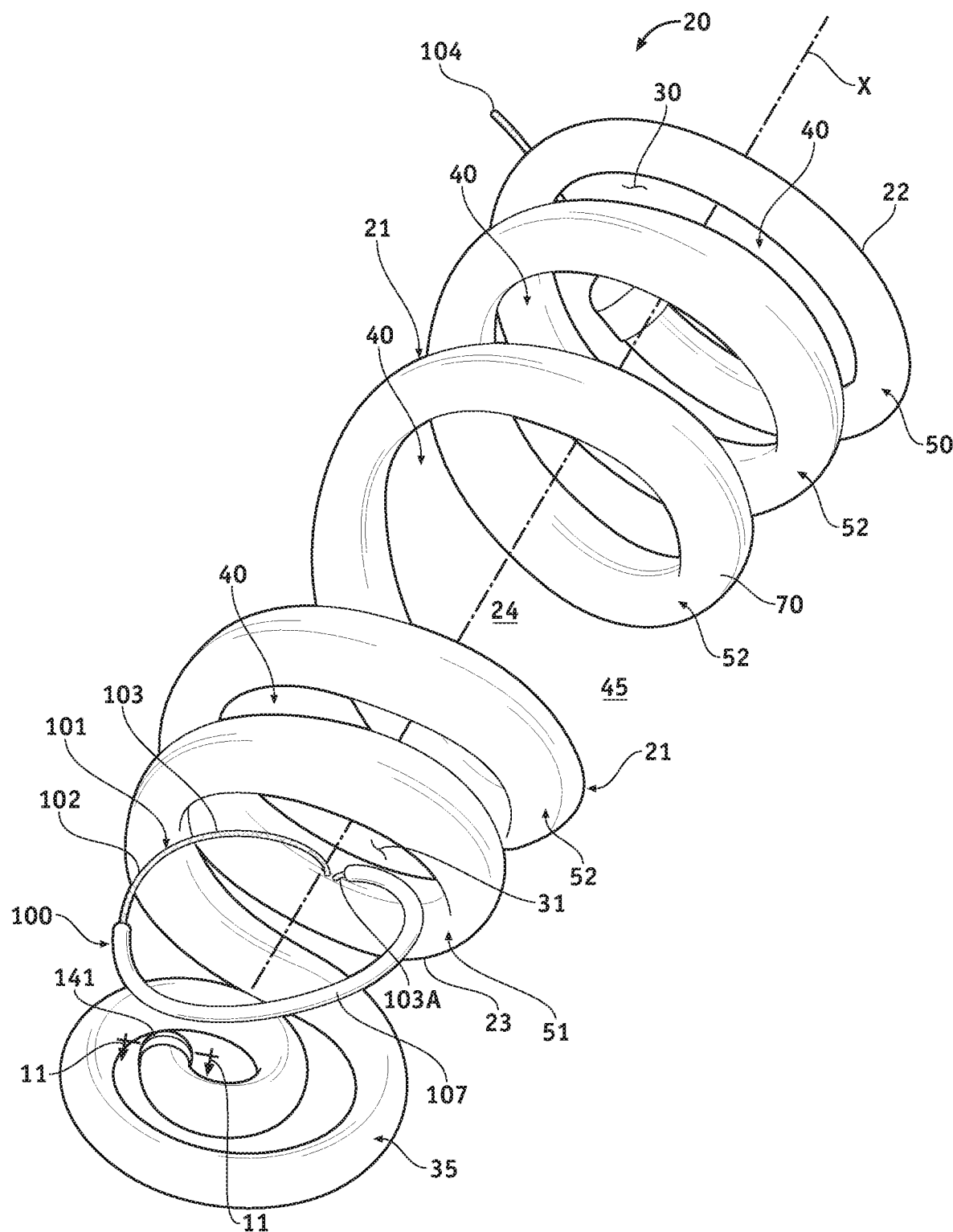
FIG. 1 is a front perspective view of a brace assembly constructed and arranged in accordance with the principle of the invention.
Figure 2:
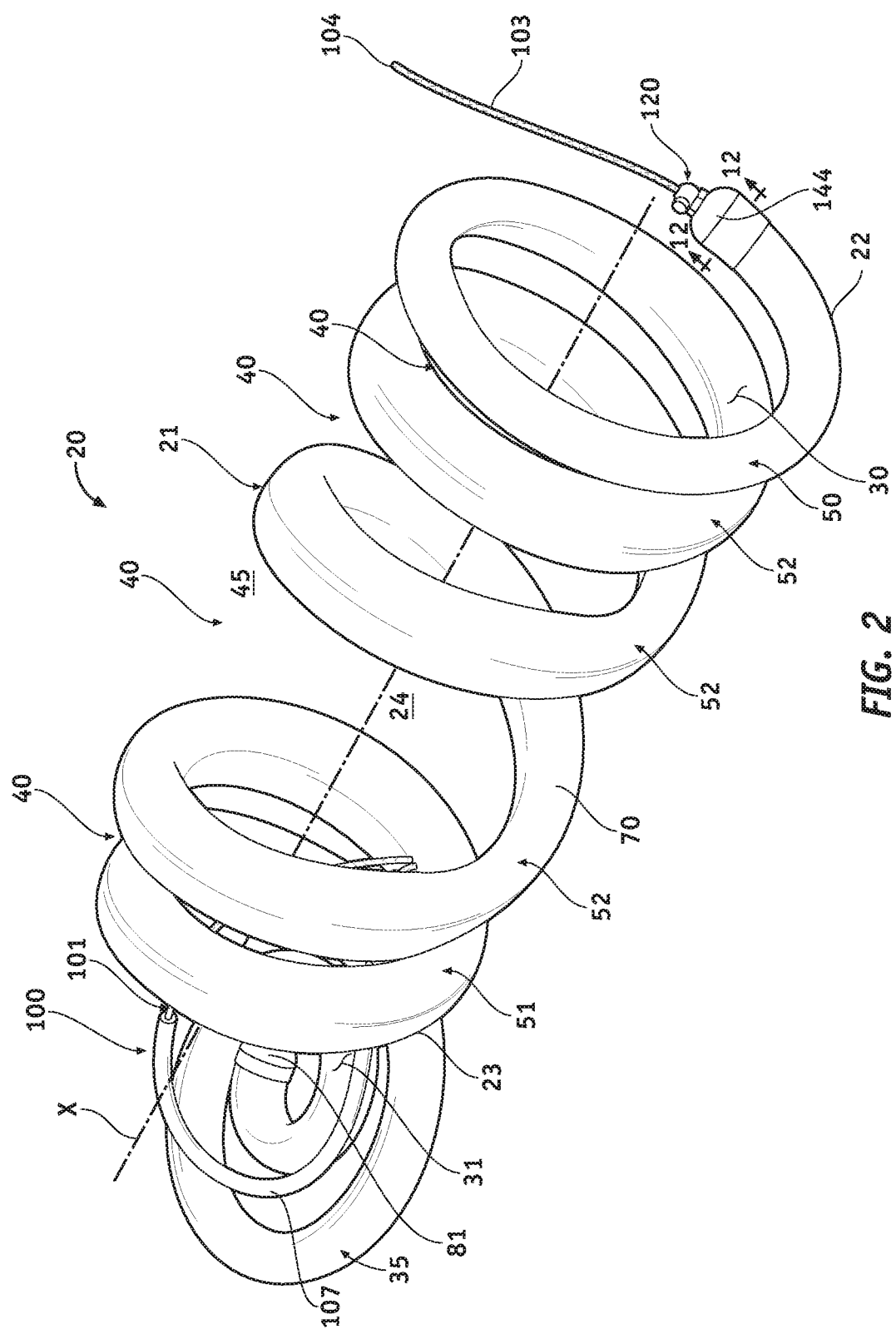
FIG. 2 is a rear perspective view of the embodiment of FIG. 1.

Turning now to the drawings, in which like reference characters indicate corresponding elements throughout the several views, attention is first directed to FIG. 1-4 in which there is seen brace assembly 20 for releasably securing and bracing an appendage in need of bracing, such as an arm of a subject, including openwork 21 having proximal extremity 22, distal extremity 23, and volume 24. Openwork 21 defines volume 24, which is between proximal extremity 22 and distal extremity 23. Proximal extremity 22 and distal extremity 23 are each open, each being open to volume 24. Proximal extremity 22 is open in that it defines proximal opening 30 to volume 24. Distal extremity 23 is open in that it defines distal opening 31 to volume 24. Accordingly, proximal extremity 22 can be referred to as an open proximal extremity, and distal extremity 23 can be referred to as an open distal extremity.

Openwork 21 is elongate longitudinally from proximal extremity 22 to distal extremity 23 and additionally from proximal opening 30 to distal opening 31. Proximal opening 30 and distal opening 31 are axially aligned. Openwork 21 is arranged about longitudinal axis X from proximal opening 30 to distal opening 31. Openwork 21 is formed with support 35, which extends outwardly from distal extremity 23, and from distal opening 31. Support 35 is for supporting a part of an appendage placed thereon, such as a hand of an arm when a forearm of the arm is applied to volume 24 through proximal opening 30 of proximal extremity 22 and when the hand of the arm extends outwardly through distal opening 31 over support 35.

Openwork 21 is a frame that is stiff, being rigid and not easily bent, and inarticulate, being "jointless" by having no articulation or joint by design. Openwork 21 defines access points 40 to volume 24 from proximate to proximal extremity 22 to proximate to distal extremity 23. Access points 40 provide direct access therethrough to an appendage applied to volume 24 through opening 30 of proximal extremity 22 without interference from openwork 21, according to the invention.

Openwork 21 is helical from proximal extremity 22 to distal extremity 23, and additionally from proximal opening 30 to distal opening 31. Openwork 21 is, therefore, a helical openwork, and includes proximal coil 50, distal coil 51, and a plurality of intermediate coils 52, three in this example, between proximal coil 50 and distal coil 51. Consistent with this disclosure, openwork 21 can include less or more than three intermediate coils 52.

Figure 4:
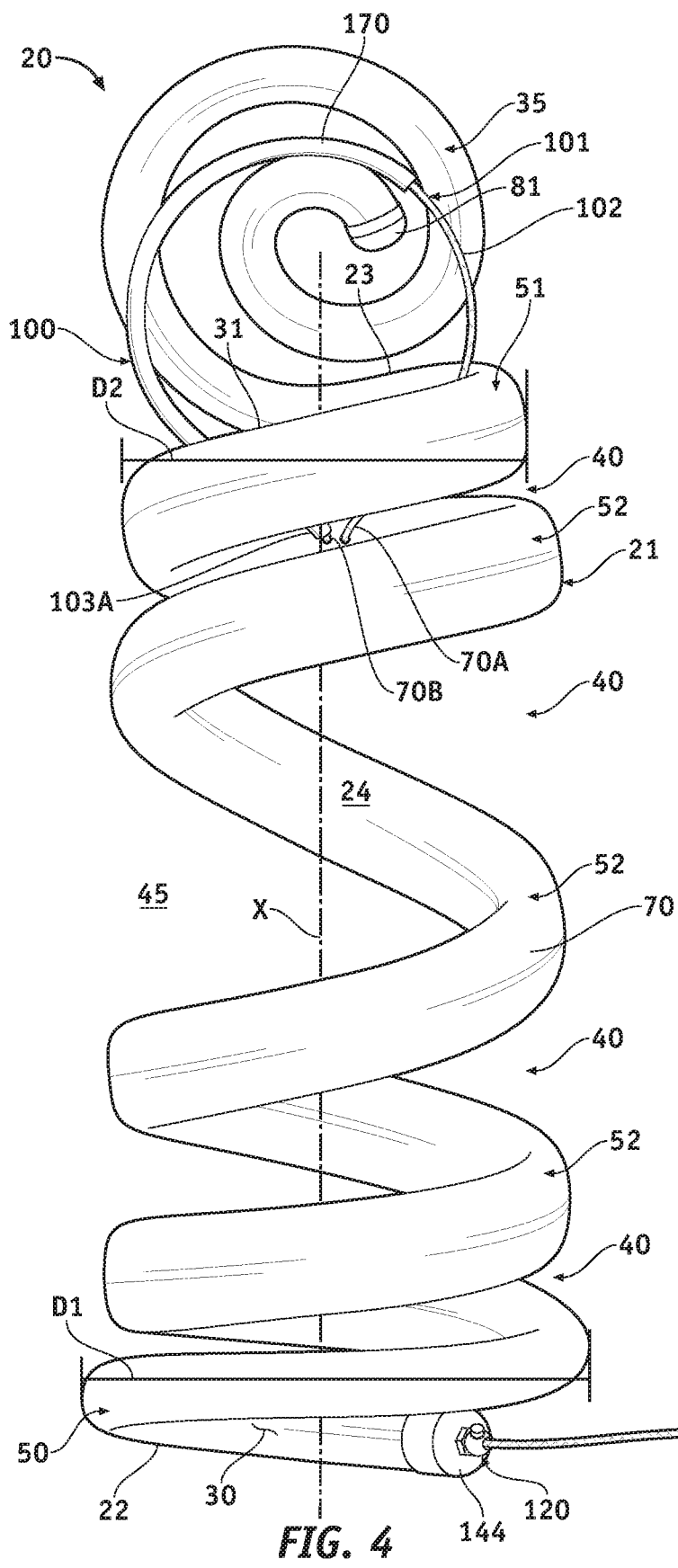
FIG. 4 is a top plan view of the embodiment of FIG. 1.

The various coils of openwork each has a diameter. In FIG. 4, proximal coil 50 has diameter D1, and distal coil 51 has diameter D2. Diameter D1 is slightly larger than diameter D2, and the diameters of the several intermediate coils 52 are slightly incrementally graduated. Accordingly, openwork 21 is slightly tapered from proximal extremity 22 to distal extremity 23 having a slightly frusto-conical shape from proximal extremity 22 to distal extremity 23 having a larger inner end defined by proximal coil 50 at proximal extremity 22 and a somewhat smaller outer end defined by distal coil 51 at distal extremity 23.

With continuing reference to FIGS. 1-4, proximal coil 50, distal coil 51, and the several intermediate coils 52 define a hollow core or volume 24 within openwork 21. Volume 24 extends from proximal extremity 32 to distal extremity 33 and additionally from proximal opening 30 to distal opening 31. Since openwork 21 is slightly tapered from proximal extremity 22 to distal extremity 23 having a slightly frusto-conical shape from proximal extremity 22 to distal extremity 23 having a larger inner end defined by proximal coil 50 at proximal extremity 22 and a somewhat smaller outer end defined by distal coil 51 at distal extremity 23, volume 24 is also correspondingly slightly tapered from proximal extremity 22 to distal extremity 23 having a slightly frusto-conical shape from proximal opening 30 at proximal extremity 22 to distal opening 31 at distal extremity 23.

Openwork 21 extends longitudinally from proximal coil 50 defining proximal opening 30 to distal coil 51 defining distal opening 31, defines volume 24 from proximal opening 30 to distal opening 31, is stiff, being rigid and not easily bent, and is inarticulate, having no articulation or joint and thereby being jointless, along its extent from and including proximal coil 50 to and including distal coil 51 and additionally from proximal opening 30 to distal opening 31. The various coils 50, 51, and 52 of openwork 21 define helical space 45 along the length of openwork 21 from proximal coil 50 to distal coil 51. Helical space 45, in turn, defines access points 40 to volume 24 between proximal coil 50 and distal coil 51 for enabling direct access therethrough to an appendage in volume 24 between proximal coil 50 and distal coil 51 when the appendage is applied to volume 24 through proximal opening 30 between proximal coil 50 and distal coil 51 and, more particularly, between proximal opening 30 and distal opening 31.

Figure 3:
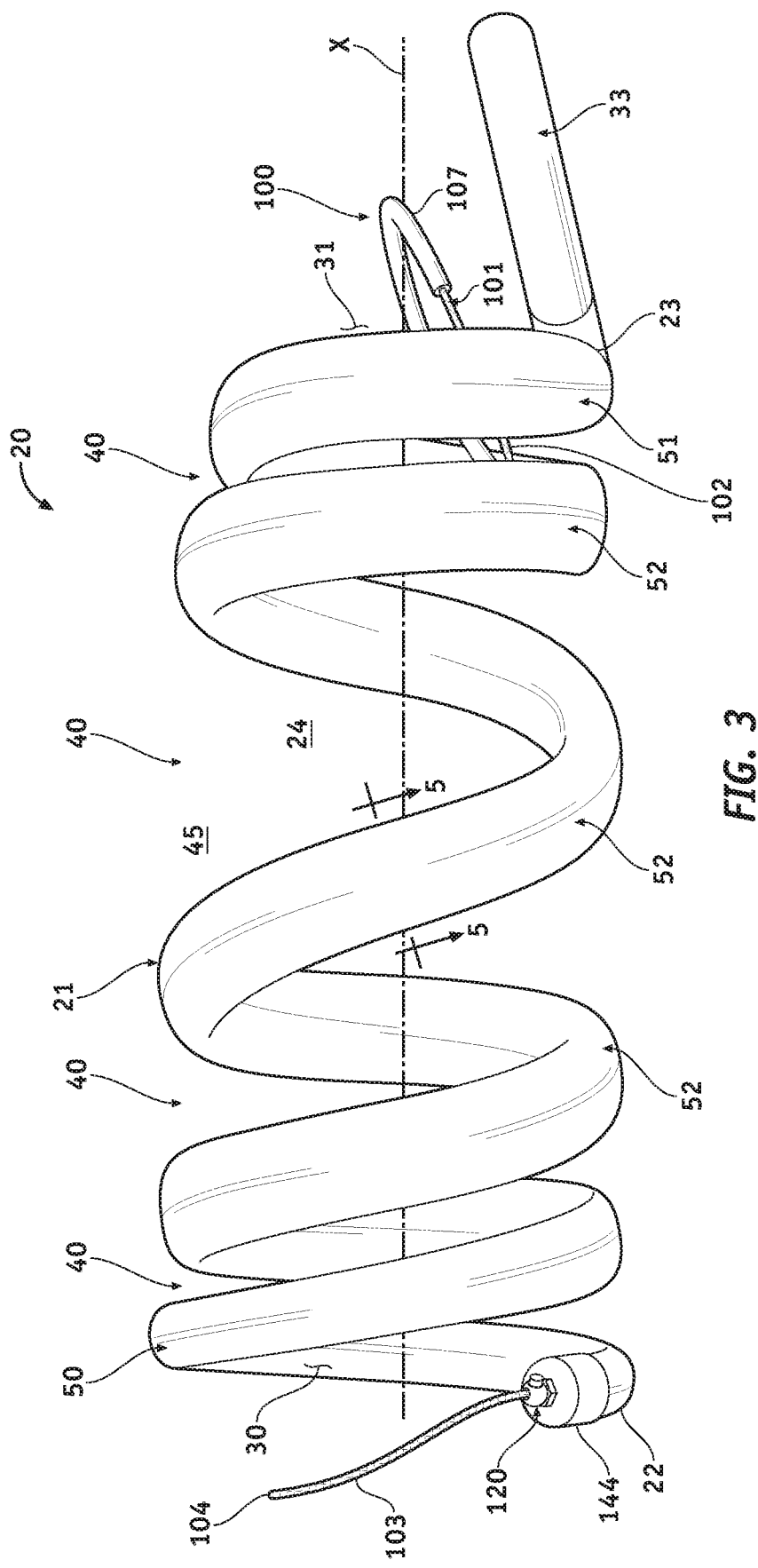
FIG. 3 is a side elevation view of the embodiment of FIG. 1.
Figure 5:
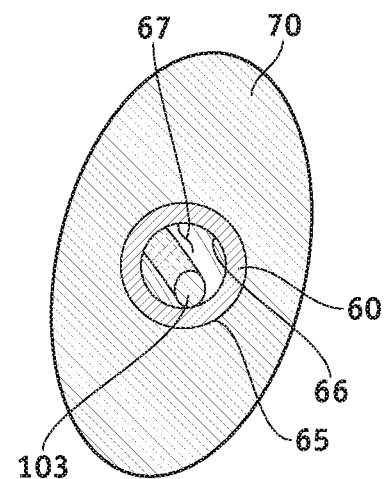
FIG. 5 is a section view taken along line 5-5 of FIG. 3.

FIG. 5 is a section view of openwork 21 taken along line 5-5 of FIG. 3. Referring to FIG. 5, openwork 21, including coils 50-52 and support 35 in FIGS. 1-4, is fabricated of a single length or strand of a hollow, cylindrical conduit 60 that extends from inner end 61 of conduit 60 in FIG. 12 to outer end 62 of conduit 60 in FIG. 11. Conduit 60 is fabricated of an inherently stiff material, a material that is inherently rigid and not easily bent, such as steel, aluminum, or other chosen material of combination of materials having the described inherently stiff material characteristics, which makes openwork 21 inherently strong, and easy, efficient, and inexpensive to manufacture. The helical design of openwork 21 is, therefore, particularly advantageous as being inherently strong and easy to manufacture. Accordingly, openwork 21 extends longitudinally from proximal coil 50 defining proximal opening 30 to distal coil 51 defining distal opening 31, defines volume 24 from proximal opening 30 to distal opening 31, is stiff, being rigid and not easily bent, and is inarticulate, having no articulation or joint and thereby being jointless, along its entire extent from and including proximal coil 50 to and including distal coil 51, additionally from and including inner end 61 to and including outer end 62, and yet additionally from proximal opening 30 to distal opening 31, according to the principle of the invention.

Figure 11:
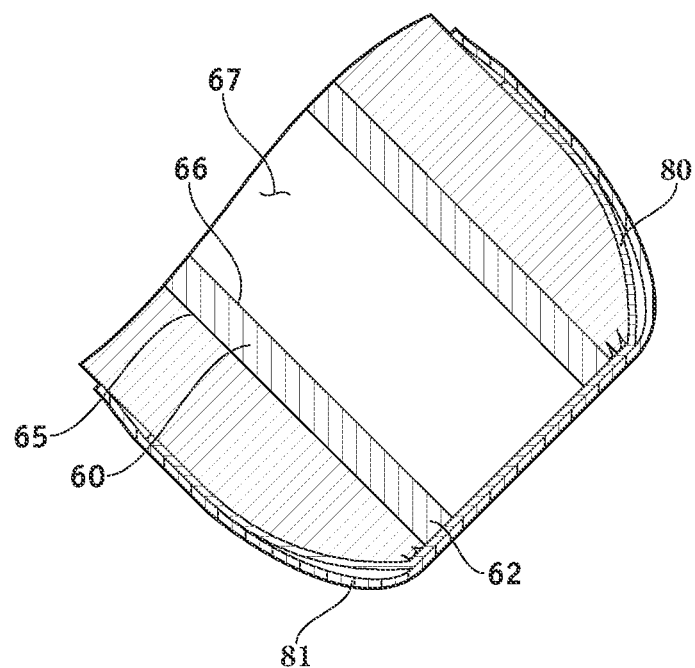
FIG. 11 is a section view taken along line 11-11 of FIG. 1.
Figure 12:
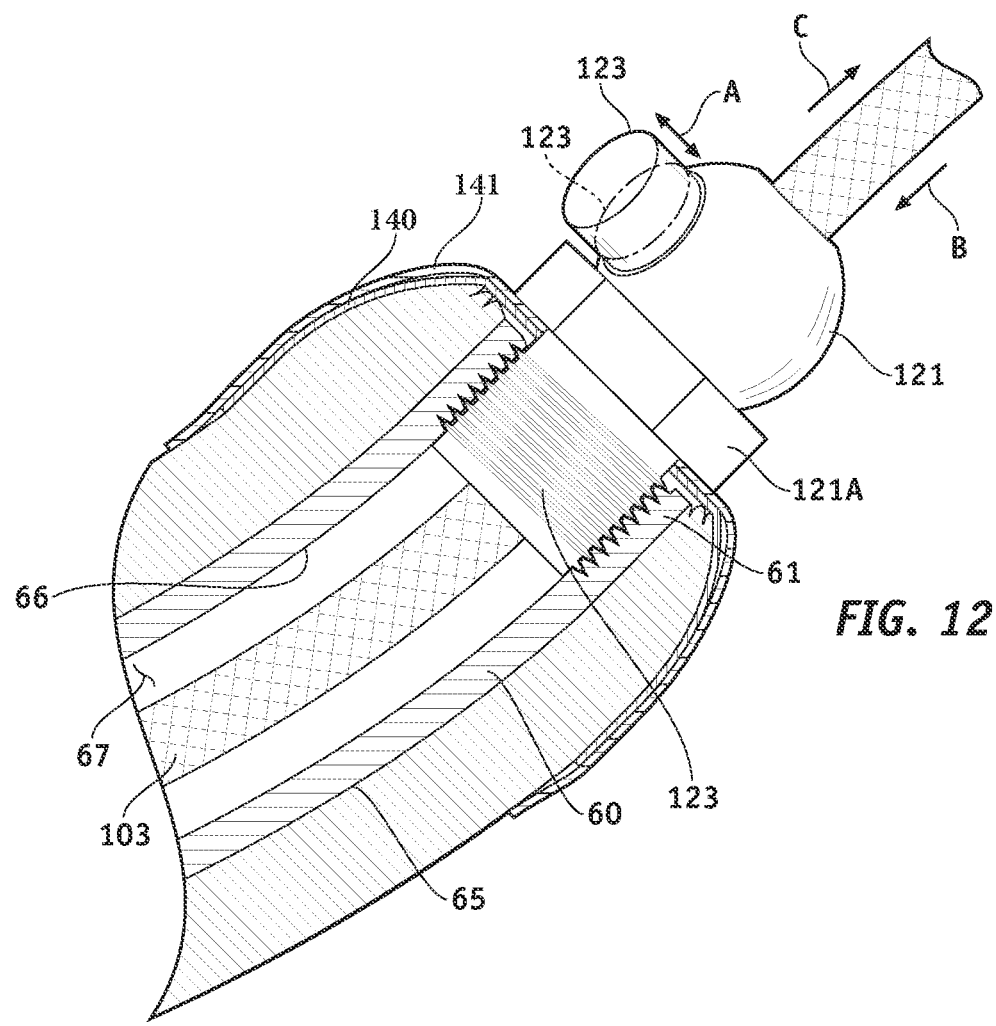
FIG. 12 is a partial section view taken along line 12-12 of FIG. 2.

Conduit 60 is padded exteriorly for comfort with padding 70 along the length of conduit 60 from inner end 61 of conduit 60 in FIG. 12 to outer end 62 of conduit 60 in FIG. 11. Conduit 60 is shaped to form coils 50-52 and support 35, and conduit 60 is padded with padding 70 form coils 50-52 and support 35. The cross section of openwork 21 in FIG. 5 is structurally the same from inner end 61 of conduit 61 in FIG. 12 to the outer end 62 of conduit 60 in FIG. 11.

Conduit 60 includes outer surface 65 and inner surface 66 that defines channel 67 through the length of conduit 60 from inner end 61 in FIG. 12 to outer end 62 in FIG. 11. Padding 70 is a soft material, such as foam or cloth padding, and is in a form of a sleeve, i.e. a padded sleeve, that circumscribes, and that is in direct contact against, outer surface 65 from inner end 61 of conduit 60 in FIG. 12 to outer end 62 of conduit 60 in FIG. 11. Accordingly, padding 70 encapsulates and enclosed conduit 60 from inner end 61 in FIG. 12 to outer end 62 in FIG. 11, and conduit 60 extends through padding 70 from inner end 61 in FIG. 12 to outer end 62 in FIG. 11.

Conduit 60 padded with padding 70 between inner end 61 and outer end 62 in FIG. 5 define openwork 21 from proximal coil 50 at proximal extremity 22 to distal coil 51 at distal extremity 23, and support 35 that extends outwardly from distal coil 52 of proximal extremity 22. Support 35 is a flat coil that extends outwardly from distal coil 51 that defines distal extremity 23, and from distal opening 31. Support 35 coils inwardly to outer end 62 in FIG. 11, and is slightly inclined upwardly in FIG. 3 being oblique to longitudinal axis X. In FIG. 11, outer end 62 and a portion of padding 70 proximate to outer end 62 are capped exteriorly with protective cap 80 of metal, plastic, or other material or combination of materials having inherently rugged and resilient material characteristics, which, in turn, is capped exteriorly with protective cap 81 of rubber, silicone, or other material or combination of materials having inherently rugged, flexible, elastic, and fluid-impervious material characteristics thereby fluid isolating outer end 62 of conduit 60.

In FIGS. 1-4, brace assembly 20 further includes restraint 100. Restraint 100 is carried by openwork 21, and is for restraining appendage 90 from being withdrawn from volume 24 through proximal opening 30 of proximal extremity 22, when restraint 100 is releasably secured to appendage 90 applied to volume 24 through proximal extremity 22, i.e. through proximal opening 30 of proximal extremity 22, in FIGS. 9 and 10, and for enabling appendage 90 for being withdrawn from volume 24 through open proximal extremity 22, i.e. through proximal opening 30, without interference from openwork 21 or restraint 100, when restraint 100 is released from appendage 90 applied to volume 24 through open proximal extremity 22, i.e. through proximal opening 30, in FIG. 7.

In FIGS. 1-4 and 6, restraint 100 is positioned proximate to distal extremity 23, and is a noose 101. Noose 101 is repeatedly adjustable between a loosened appendage-receiving/releasing position in FIG. 7, and a comparatively constricted appendage-securing position in FIGS. 9 and 10, and to selected positions therebetween to enable noose 101 to fit around and secure appendages of varying girths.

Figure 6:
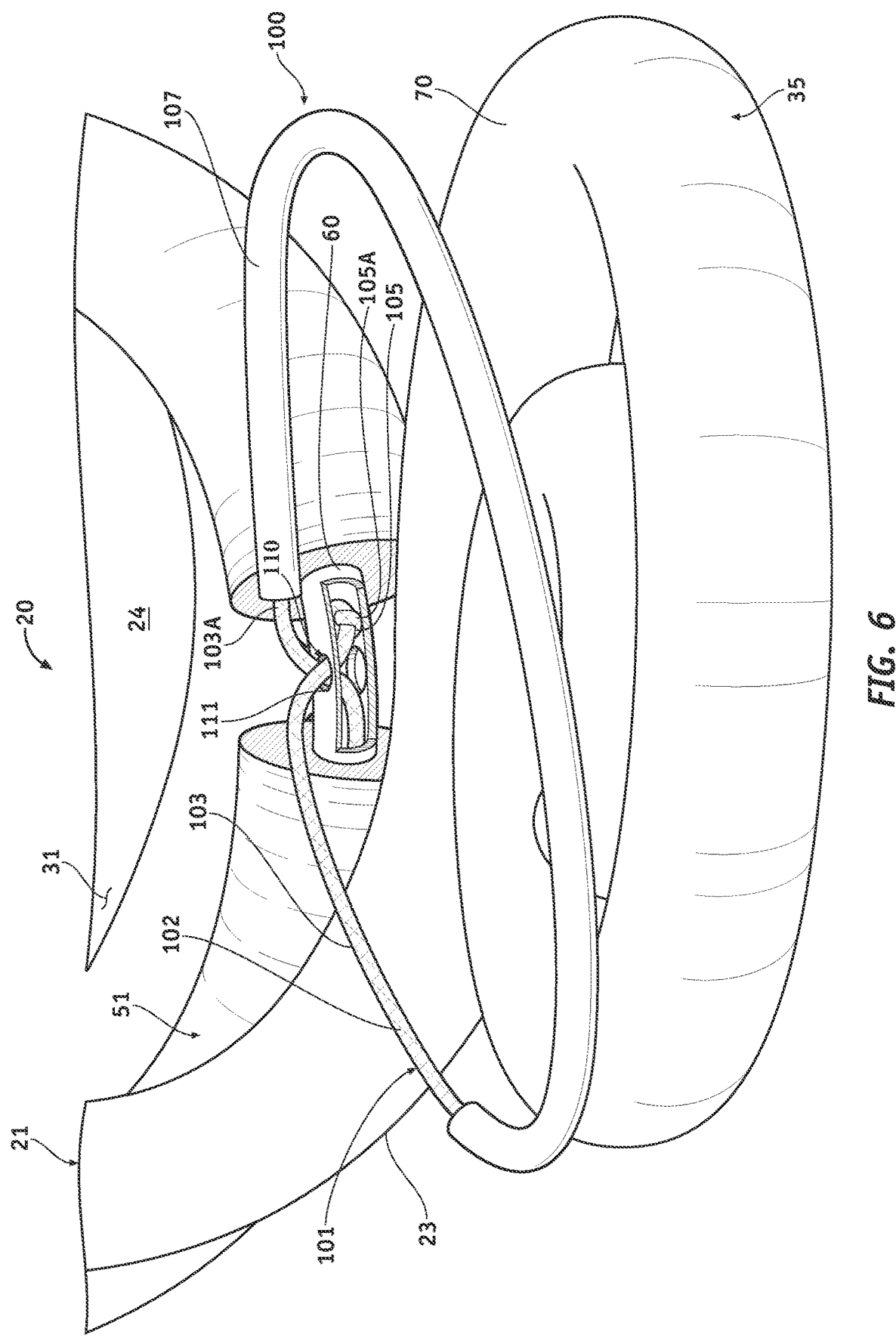
FIG. 6 is an enlarged fragmentary view of the embodiment of FIG. 1 with portions therein being broken away to better illustrate the components thereof.

Noose 101 includes loop portion 102 of line 103 and a sliding coupling, denoted generally at 110 in FIG. 6. Sliding coupling 110 loosens loop portion 102 and at the same time enables adjustment of loop portion 102 between the loosened appendage-receiving/releasing position, as is shown by example in FIG. 7, and the comparatively constricted appendage-securing position, as is shown by example in FIGS. 9 and 10. Line 103 is a flexible and durable rope or cord, and includes inner end 104 in FIGS. 1-4, and outer end 105 in FIG. 6. In FIG. 6, outer end 105 is in channel 67 of the portion of conduit 60 defining distal coil 51 near the base of support 35, and is formed into knot 105A. Since outer end 105 is formed with knot 105A, outer end 105 is a knotted outer end of line 103. Opening 111 is formed through the part of conduit 60 of distal coil 51 at the base of support 35. Line 103 extends outwardly through opening 111 from knot 105A in channel 67 and through opening 70A (FIG. 4) through padding 70 to loop portion 102, and back into channel 67 from a standing part 103A of line 103 of loop portion 102 through opening 70B (FIG. 4) through padding 70 and back through opening 111 to channel 67 in FIG. 5 and through channel 67 through conduit 60 from opening 111 of distal coil 51 in FIG. 6 to inner end 61 of conduit 60 in FIG. 12 and outwardly through inner end 61 and through lock 120 to inner end 104 of line 103. Line 103 can slide through channel 67 between opening 111 and inner end 61 of conduit 60. Knot 105A is larger than opening 111, which disables knot 105A of outer end 105 from passing outwardly from channel 67 through opening 111. This secures knotted outer end 105 to conduit 60 within channel 67. Opening 111 is sufficiently small to disable knot 105A from passing outwardly from channel 67 through opening 111, and at the same time is sufficiently large to enable standing part 103A of line 103 passing inwardly through opening 111 from loop portion 102 to slide back and forth through opening 111 relative to the outgoing line 103 extending to loop portion 102 through opening 111 from knot 105A of outer end 105 of line 103. This enables the adjustment of loop portion 102 of noose 101 between the loosened appendage-receiving/releasing position, shown by way of example in FIG. 7, and the comparatively constricted appendage-securing position, shown by way of example in FIGS. 9 and 10. Sliding coupling 110 is defined by opening 111 that concurrently captures line 103 passing outwardly through opening 111 from knot 105A secured in channel 67 and to loop portion 102, and standing part 103A of line 103 passing inwardly through opening 111 into channel 67 from loop portion 102, according to the invention.

In FIGS. 1-4 and 6, a length of line 103 forming loop portion 102 of noose 101 is padded exteriorly for comfort with padding 107. Padding 107 is a soft material, such as foam or cloth, and is in a form of a sleeve, i.e. a padded sleeve, that circumscribes a length of line 103 forming loop portion 102. In other words, a length of line 103 forming loop portion 102 extends through padding 107. Loop portion 102 of line 103 through padding 107 can slide through padding 107, which enables loop portion 102 of line 103 to automatically slide through padding 107 as needed when loop portion 102 of noose 101 is adjusted in size.

Figure 7:
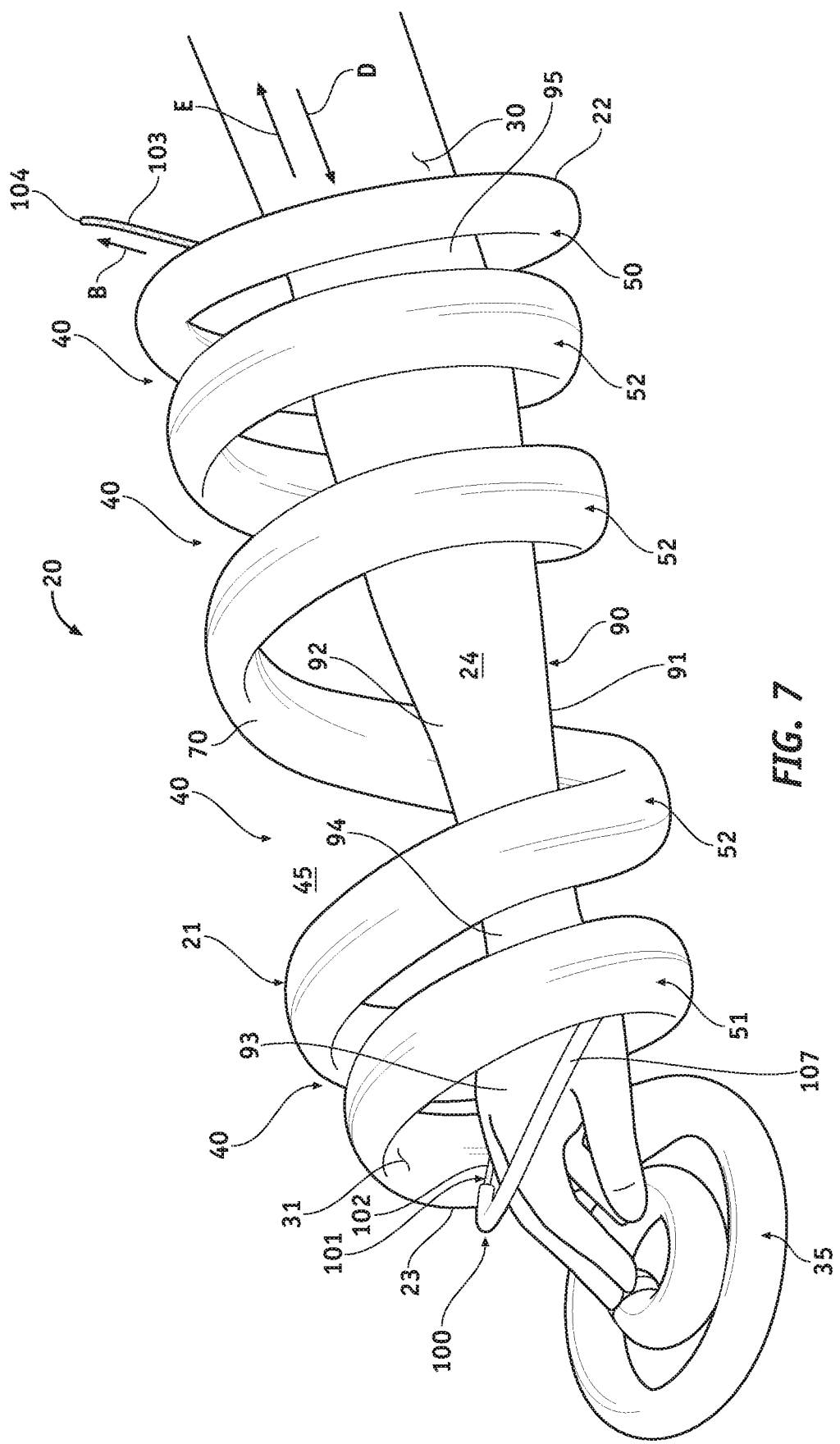
FIGS. 7-9 illustrate a sequence of events for bracing an appendage with the brace assembly first illustrated in FIG. 1.
Figure 9:
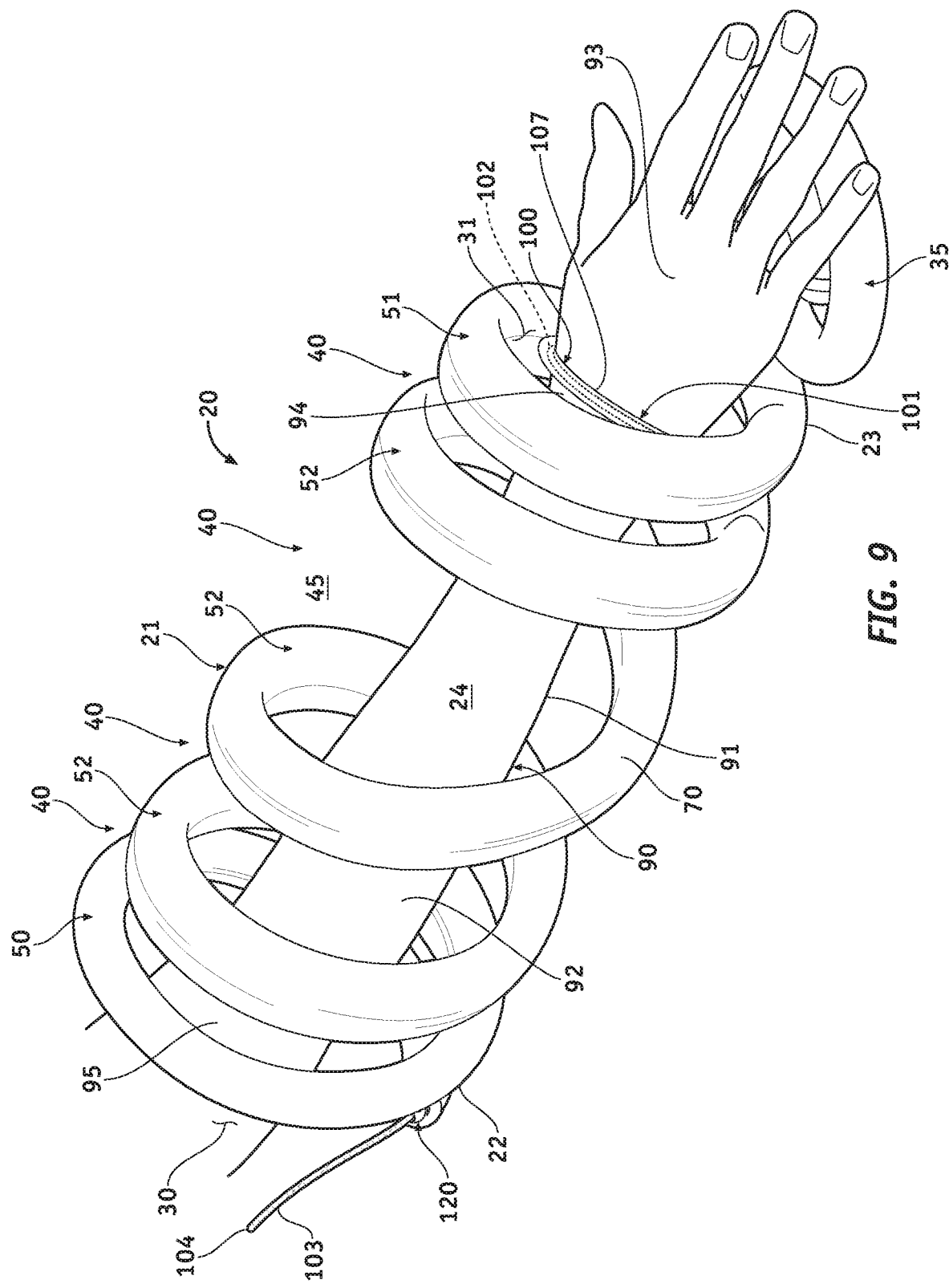
Figure 10:
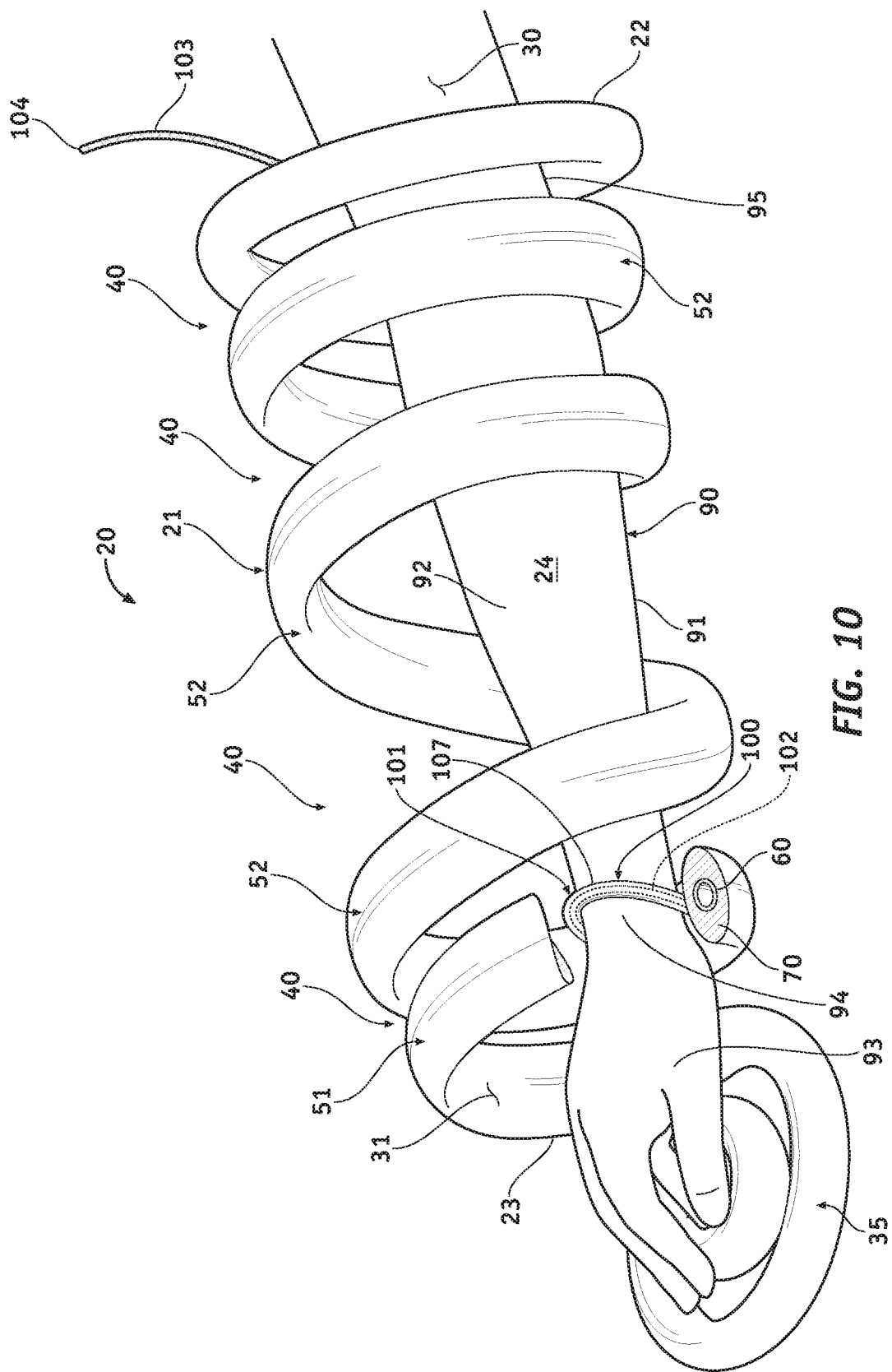
FIG. 10 is a view corresponding to FIG. 9 with portions of the brace assembly being broken away to better illustrate the application of the appendage therein.

Lock 120 is operatively coupled to line 103 for releasably securing line 103 relative to openwork 21 for disabling line 103 from sliding through channel 67 for selectively securing noose 101 in the loosened appendage-receiving/releasing position of loop portion 102 in FIG. 7, the comparatively constricted appendage-securing position of loop portion 102 in FIGS. 9 and 10, and at selected positions therebetween to enable loop portion 102 of noose 101 to fit around and secure appendages of varying girths, and releasing line 103 for enabling line 103 to slide through channel 67 for enabling adjustment of noose 101 between the loosened appendage-receiving/releasing position of loop portion 102 in FIG. 7 and the comparatively constricted appendage-securing position of loop portion in FIGS. 9 and 10.

Lock 120 is carried by openwork 21 proximate to proximal extremity 22. In this embodiment, lock 120 is carried by proximal coil 50 and, more particularly by inner end 61 of conduit 60 shown in FIG. 12 that forms proximal coil 50. Line 103 extends through and is enclosed within channel 67 of conduit 60 (FIG. 5) of openwork 21 from sliding coupling 110 in FIG. 6 to lock 120 carried by inner end 61 of conduit 60 in FIG. 12, and through inner end 61 of conduit 60 and through lock 120 to inner end 104 of line 103 in FIGS. 1-4.

In FIG. 12, lock 120 is a conventional, spring-loaded cord lock, the details of which are well-known and are discussed only to an extent sufficient to describe how lock 120 works in conjunction with line 103 and noose 101. Lock 120 includes housing 121 releasably secured to inner end 61 of conduit 60 of openwork 21. Housing 121 is fashioned with the customary spring-loaded button 123 movable in reciprocal directions indicated by double arrowed line A in FIG. 12 between a locked position defining a locked position of lock 120 for securing line 103 disabling line 103 from sliding through housing 121 for securing loop portion 102 of noose 101, and a dotted line released position in FIG. 12 defining an unlocked position of lock 120 for releasing line 103 for enabling line 103 to slide through housing 121 for enabling loop portion 102 of noose 101 to be selectively adjusted between its loosened appendage-receiving/releasing position in FIG. 7 and its comparatively constricted appendage-securing position in FIGS. 9 and 10. Accordingly, lock 120 is operatively coupled to line 103 for repeatedly and selectively securing line 103 for securing loop portion 102 of noose 101, and releasing line 103 for un-securing loop portion 102 of noose 101.

When lock 120 is in its locked position in FIG. 12 securing line 103, the length of line 103 through channel 67 of conduit 60 from lock 120 to sliding coupling 110 is secured, i.e. fixed. This disables line 103 from being slid through channel 67, which inherently secures loop portion 102 of noose 101 in response by disabling loop portion 102 from being size adjusted via sliding coupling 110 between its loosened appendage-receiving/releasing position in FIG. 7 and its comparatively constricted appendage-securing position in FIGS. 9 and 10 by sliding line 103 through channel 67. When lock 120 is in its unlocked position indicated by the dotted line position of button 123 in FIG. 12, the length of line 103 through channel 67 of conduit 60 from lock 120 to sliding coupling 110 is unsecured, i.e. unfixed. This enables line 103 to be slid through channel 67, which inherently releases or un-secures loop portion 102 of noose 101 in response by enabling loop portion 102 to be adjusted in size via sliding coupling 110 between its loosened appendage-receiving/releasing position in FIG. 7 and its comparatively constricted appendage-securing position in FIGS. 9 and 10.

To adjust loop portion 102 of line 103 from the loosened appendage-receiving/releasing position in FIG. 7 when lock 120 is in its unlocked position, line 103 extending outwardly from lock 120 to inner end 104 is pulled, such as by hand, outwardly through lock 120 in the direction of arrowed line B in FIG. 12 sliding line 67 through channel in a direction from opening 111 to inner end 61 until loop 102 of noose 101 is sufficiently constricted to the comparatively constricted appendage-securing position in FIGS. 9 and 10. To adjust loop portion 102 of line 103 from the constricted appendage-securing position in FIGS. 9 and 10 when lock 120 is in its unlocked position, standing part 103A of line 103 of loop 102 is pulled, such as by hand, inwardly through lock 120 in the direction of arrowed line C in FIG. 12 sliding line 67 through channel in a direction from inner end 61 to opening 111 until loop 102 of noose 101 is sufficiently loosened to the comparatively loosened appendage-receiving/releasing position in FIG. 7.

In this example, inner end 61 of conduit 60 is internally threaded, and housing 121 is formed with outwardly threaded nipple 124 threaded into internally threaded inner end 61 of conduit 60 via rotation releasably securing/ connecting housing 121 of lock 120 to inner end 61 of conduit 60 of openwork 21. The internally threaded inner end 61 of conduit 60 is an engagement element of an engagement pair, and the externally threaded nipple 124 of lock 120 is a detachably engageable complemental engagement element of the engagement pair for releasably securing lock 120 to inner end 61 of conduit 60 of openwork 21. The skilled artisan will readily appreciate that other forms of engagement pairs can be used to releasably secure lock 120 to inner end 61 of conduit 60 of openwork 21 without departing from the invention, such as snap engagement pairs, detent engagement pairs, or the like.

In FIG. 12, inner end 61 of conduit 60 and a portion of padding 70 proximate to inner end 61 are capped exteriorly with protective cap 140 of metal, plastic, or other material or combination of materials having inherently rugged and resilient material characteristics, which, in turn, is capped exteriorly with protective cap 144 of rubber, silicone, or other material or combination of materials having inherently rugged, flexible, elastic, and fluid-impervious material characteristics. In this example caps 140 and 144 are formed with central openings 141 and 145, respectively, which are axially aligned. Threaded nipple 124 extends through openings 141 and 145 and is threaded via rotation of lock 120 to internally-threaded inner end 61 of conduit 60, and base 121A of housing 121 is tightened via rotation of lock 120 against cap 144 capping cap 140 thereby securing caps 140 and 144 while at the same time forming a fluid-impervious seal between base 121A of housing 121 and inner end 61 of conduit 60 fluid isolating inner end 61 of conduit 60.

Brace assembly 20 is useful for releasably securing and bracing appendage 90 in FIGS. 7-10 in need of bracing, which in this example is arm 91, being a right arm in this example, between elbow 95 and hand 93 of arm 91. In use, loop 102 of noose 101 is set to its loosened appendage-receiving/releasing position in FIG. 7 and arm 91 is inserted hand 93 first into volume 24 through proximal opening 30 in the direction of arrowed line D and is advanced through volume 24 in this direction of arrowed line D until hand 93 reaches distal extremity 23 and emerges through distal opening 31 over support 35 and elbow 95 reaches proximal opening 30. Openwork 21 is sized to relate to arm 91 in this way. Volume 24 is sufficiently large to enable hand 93 and forearm 92 of arm 91 to elbow 95 to be inserted therein as described without coils 50-52 of openwork 21 being tightened thereagainst, which enables hand 93 and forearm 92 of arm 91 to be applied through volume 24 through proximal opening 30 and withdrawn from volume 24 through proximal opening 30 when arm 91 is free from restraint 100. At the same time, volume 24 is sufficiently small to enable coils 50-52 of openwork 21 to brace forearm 92 and restrict movement of forearm 92. Openwork 21 is sufficiently long from proximal extremity 22 to distal extremity 23 to enable openwork 21 to extend along substantially the entire length of forearm 92 from proximal extremity 22 to distal extremity 23 when hand 93 is positioned over support 35 through distal opening 31 at distal extremity 23. Further, the slightly frusto-conical shape of volume 24 enables volume 24 to relate the inherently tapered shaped of forearm 91 from elbow 95 to wrist 94, according to the invention.

Figure 8:
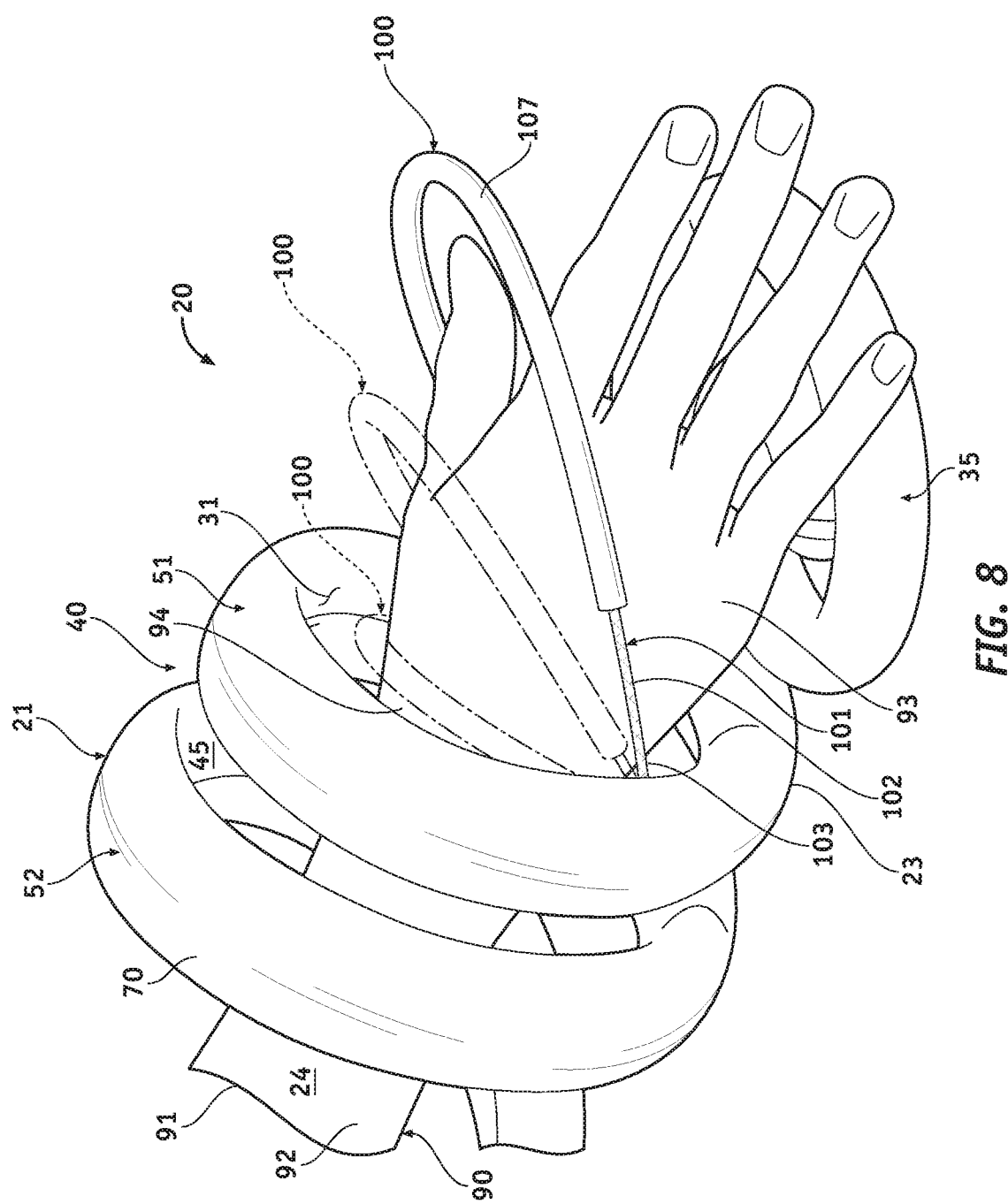

Loop portion 102 of noose 101, being in its initial loosened appendage-receiving/releasing position, is looped over hand 93 in FIGS. 7 and 8. In FIG. 12, button 123 is pressed to its dotted line unlocked position releasing line 103 from lock 120. Line 103 is pulled through lock 120 and through channel 67 of conduit 60 in the direction from sliding coupling 110 to inner end 61 by pulling the portion of line 103 extending outwardly from lock 120 to inner end 104 in the direction of arrowed line B in FIGS. 7 and 12 to adjust loop 102 of noose 101 via sliding coupling 110 from its loosened appendage-receiving/releasing position in FIGS. 7 and 8 to the comparatively constricted appendage-securing position in FIGS. 9 and 10 constricting and tightening loop portion 102 of noose 101 around the girth of wrist 94 of arm 91 thereby releasably securing the girth of wrist 94 of arm 91 between hand 93 and forearm 92, at which point button 123 is released.

When button 123 is released, the spring loading of button 123 automatically shifts button 123 from its dotted line unlocked position in FIG. 12 to its locked position in FIG. 12 securing line 103 to lock 120, which automatically secures the length of line 103 through channel 67 of conduit 60 from lock 120 to sliding coupling 110 thereby releasably securing loop portion 102 of noose 101 in response about wrist 94 of arm 91 and securing arm 91 to brace assembly 20. The tightening of loop portion 102 of noose 101 about wrist 94 and the secured length of line 103 through channel 67 of conduit 60 of openwork 21 from lock 120 to sliding coupling 110 secures wrist 84 and disables or otherwise restrains arm 91 from being withdrawn from volume 24 through opening 30 of proximal extremity 22, while padding 107 provides comfort against wrist 94. As a result, if the person tries to withdraw her arm 91 from volume 24, loop portion 102 of noose 101 which is too small for hand 93 to pass through and which is tightened around wrist 94 and secured at lock 120 locked against line 103 pulls against wrist 94 between hand 93 and forearm 92, which prevents hand 93 from being pulled into volume 24 through distal opening 31 and restrains arm 91 from being withdrawn from volume 24 through proximal opening 30. At the same time, the stiff, and inarticulate, i.e. jointless, design characteristics of openwork 21 from proximal extremity 22 defining proximal opening 30 to distal extremity 23 defining distal opening 31 are particularly advantageous because they cooperate to brace forearm 92 and restrain/prevent arm 91 in volume 24 from bending, while the jointless design has no pinch points that joints and articulations have than can pinch arm 91, while the positioning of support 35 enables hand 93 to rest on support 35 in FIG. 9 for comfort. At the same time, access points 40 to volume 24 between proximal extremity 22 and distal extremity 23 defined by helical space 45 provide direct access therethrough to forearm 92 extending through volume 24 between proximal coil 50 of proximal extremity 22 and distal coil 51 of distal extremity 23 for enabling a caregiver to administer therapy, topical preparations, shots, or treatment to forearm 92 via access points 40. The exterior padding of openwork 21 provides comfort to arm 91 when arm 91 is braced by brace assembly 20. Furthermore, the helical design of openwork 21 is particularly advantageous for not completely enclosing arm 91 applied to volume 24, for enabling air to circulate around arm 91 applied to volume for comfort, and for enabling access to arm 91 in volume 24 for treatment/therapeutic purposes, according to the principle of the invention.

The stiff and inarticulate, i.e. jointless, characteristics of openwork 21 are advantageous/important for bracing arm 91 and restraining arm 91 from bending in volume 24 when arm 91 is applied to and secured in volume 24, such as when arm is injured or otherwise in need of being braced and restrained from bending, according to the invention. The stiff and inarticulate, i.e. jointless, characteristics of openwork 21 are also particularly advantageous for allowing handcuffs, a zip tie, or other chosen restrain to secure openwork 21 to a frame or other object for securing an individual in place whose arm is braced and restrained by brace assembly 21. Since joints can inherently pinch an appendage and can define weak points that can be broken, the jointless characteristic of openwork 21 of brace assembly 20 is free from joints and such weak points and is, therefore, uniquely designed not to pinch an appendage and to resist breakage, according to the invention.

Noose 101 is designed to comfortably secure wrist 94 of arm 91 between hand 93 and forearm 92 and sufficiently restrain arm 91 from being withdrawn from volume 24 through proximal opening 30 and allowing hand 93 to be pulled into volume 24 through distal opening 31 when arm 91 is positioned in volume 24 and secured by noose 101. This is why noose 101 is advantageously positioned at distal extremity 23 of openwork 21 at distal coil 52, according to the invention. Further, noose 101 is a reliable restraint, and is uniquely configured to work with openwork 21 to provide an inexpensive, flexible, easily-adjustable form of restraint.

To remove arm 91 from brace assembly 20, the foregoing operation for bracing and securing arm 91 with brace assembly 20 need only be reversed. When loop 102 of noose 101 is adjusted from the constricted appendage-securing position in FIGS. 9 and 10 back to the loosened appendage-receiving/releasing position in FIGS. 7 and 8, being released from arm 91, arm 91 is enabled for being withdrawn from volume 24 through open proximal extremity 22, i.e. through proximal opening 30 of proximal extremity 22, without interference from openwork 21. To withdraw arm 91 from volume 24, button 123 is depressed to its dotted line unlocked position releasing line 103 from lock 120. Line 103 is pulled through lock 120 and through channel 67 in the direction from inner end 61 to opening 111 by pulling standing part 103A of line 103 of loop portion 102 of noose 101 in the direction of arrowed line C in FIG. 12 to adjust loop 102 of noose 101 via sliding coupling 110 from its constricted appendage-securing position in FIGS. 9 and 10 tightened and secured around wrist 94 to its loosened appendage-receiving/releasing position in FIGS. 7 and 8 causing loop portion 102 of noose 101 to withdraw from about and release the girth of wrist 94 of arm 91 between hand 93 and forearm 92, at which point button 123 is released. Again, when button 123 is released, the spring loading of button 123 automatically shifts button 123 from its dotted line unlocked position in FIG. 12 to its locked position in FIG. 12 securing line 103 to lock 120, which automatically secures the length of line 103 through channel 67 of conduit 60 from lock 120 to sliding coupling 110 thereby releasably securing loop portion 102 of noose 101 in response. Having withdrawn loop portion 102 of noose 101 from wrist 94 so loop portion 102 is sufficiently large to enable hand 93 to pass therethrough, hand 93 is withdrawn from loop 102 and arm 91 is withdrawn from volume 24 in the direction of arrowed line D in FIG. 7 without interference from openwork 21 and restraint 100, according to the principle of the invention.

In sum, brace assembly 20 for releasably securing and bracing an appendage in need of bracing is disclosed, which includes openwork 21 including open proximal extremity 22, distal extremity 23, and volume 24 between open proximal extremity 22 and distal extremity 23. Openwork 21 is stiff, being rigid and not easily bent, and is inarticulate, having no articulation or joint and thereby being jointless, and defines access points 40 to volume 24 from proximate to open proximal extremity 22 to proximate to distal extremity 23 for enabling access to the appendage applied to volume 24 through open proximal extremity 22. Restraint 100 is carried by openwork 21 for restraining the appendage from being withdrawn from volume 24 through open proximal extremity 22, when restraint 100 is releasably secured to the appendage applied to volume 24 through open proximal extremity 22, and for enabling the appendage for being withdrawn from volume 24 through open proximal extremity 22 without interference from openwork 24, when restraint 100 is released from the appendage applied to volume 24 through open proximal extremity 24. Restraint 100 is noose 101. Noose 101 is proximate to distal extremity 23. Noose 101 is adjustable between a loosened appendage-receiving/releasing position and a comparatively constricted appendage-securing position. Noose 101 includes loop portion 102 of line 103 and sliding coupling 110 closing loop portion 102. Lock 120 is for releasably securing line 103 relative to openwork 21 for securing loop portion 102. Lock 120 is carried by openwork 21, and line extends from loop portion 102 through sliding coupling 110 and to lock 120. Line 103 extends through openwork 21 from sliding coupling 110 to lock 120. Line 103 between sliding coupling 110 and lock 120 is enclosed within openwork 21. Lock 120 is proximate to open proximal extremity 22. Lock 120 is operatively coupled to line 103 for releasably securing line 103 relative to openwork 21 for selectively securing loop portion 102 of noose 101 in the loosened appendage-receiving/releasing position, the comparatively constricted appendage-securing position, and at selected positions therebetween to enable loop portion 102 of noose 101 to fit around and secure appendages of varying girths, and releasing line 103 for enabling adjustment of loop portion 102 of noose 101 between the loosened appendage-receiving/releasing position and the comparatively constricted appendage-securing position.

According to another aspect of the invention, brace assembly 21 for releasably securing and bracing an appendage in need of bracing is disclosed, which includes helical openwork 21, and restraint 100. In this embodiment, helical openwork 21 extends longitudinally from proximal coil 50 defining proximal opening 30 to distal coil 51 defining distal opening 31, defines volume 24 from proximal opening 30 to distal opening 31, is stiff, being rigid and not easily bent, and is inarticulate, having no articulation or joint from proximal coil 50 to distal coil 51 and thereby being jointless, and defines helical space 45 from proximal coil 50 to distal coil 51 defining access points 40 to volume 24 between proximal coil 50 and distal coil 51 for enabling access to an appendage between proximal coil 50 and distal coil 51 when the appendage is applied to volume 24 through proximal opening 30. Restraint 100 is carried by helical openwork 21 for restraining the appendage from being withdrawn from volume 24 through proximal opening 30, when restraint 100 is releasably secured to the appendage applied to volume 24 through proximal opening 30, and for enabling the appendage for being withdrawn from volume 24 through proximal opening 30 without interference from helical openwork 21, when restraint 100 is released from the appendage applied to volume 24 through proximal opening 30. Restraint 100 is noose 101. Noose 101 is proximate to distal coil 51 proximate to distal opening 31. Noose 101 is adjustable between a loosened appendage-receiving/releasing position and a comparatively constricted appendage-securing position. Noose 101 includes loop portion 102 of line 103 and sliding coupling 110 closing loop portion 102. Lock 120 is for releasably securing line 103 relative to helical openwork 21 for securing loop portion 102. Lock 120 is carried by helical openwork 21, and line 103 extends from loop portion 102 through sliding coupling 110 and to lock 120. Line 103 extends through helical openwork 21 from sliding coupling 110 to lock 120. Line 103 between sliding coupling 110 and lock 120 is enclosed within helical openwork 21. Lock 120 is secured to proximal coil 50. Lock 120 is operatively coupled to line 103 for releasably securing line 103 relative to openwork 21 for selectively securing loop portion 102 of noose 101 in the loosened appendage-receiving/releasing position, the comparatively constricted appendage-securing position, and at selected positions therebetween to enable loop portion 102 of noose 101 to fit around and secure appendages of varying girths, and releasing line 103 for enabling adjustment of loop portion 102 of noose 101 between the loosened appendage-receiving/releasing position and the comparatively constricted appendage-securing position.

Brace assembly 20 is described in conjunction with bracing arm 91, specifically the outer part of a right arm between elbow 95 and hand 93, in which arm 91 in the drawings is a right arm. Brace assembly 20 is equally useful for similarly bracing other appendages, including the outer part of a left arm between the elbow and the hand of the left arm, the outer part of a right leg between the knee and the foot of the right leg, and the outer part of a left leg between the knee and the foot of the left leg. A brace assembly constructed and arranged in accordance with the principle of the invention can also be sized to a right arm between the right shoulder and the right foot of the right arm, the left arm between the left shoulder and the left foot of the left arm, the right leg between the hip to the right foot of the right leg, or the left leg between the hip and the left foot of the left leg.

The invention has been described above with reference to preferred embodiments. However, those skilled in the art will recognize that changes and modifications may be made to the embodiments without departing from the nature and scope of the invention. Various changes and modifications to the embodiment herein chosen for purposes of illustration will readily occur to those skilled in the art. To the extent that such modifications and variations do not depart from the spirit of the invention, they are intended to be included within the scope thereof.

Having fully described the invention in such clear and concise terms as to enable those skilled in the art to understand and practice the same, the invention claimed is:

1. A brace assembly configured to releasably secure and brace an appendage, comprising:
    an openwork including an open proximal extremity, a distal extremity, and a volume between the open proximal extremity and the distal extremity, the openwork is stiff, being rigid and not easily bent, and inarticulate, being jointless having no articulation or joint, and defines access points to the volume from proximate to the open proximal extremity to proximate to the distal extremity configured to enable access to the appendage applied to the volume through the open proximal extremity; and
    a restraint carried by the openwork and configured to restrain the appendage from being withdrawn from the volume through the open proximal extremity, when the restraint is configured to be secured to the appendage applied to the volume through the open proximal extremity, and configured to enable the appendage for being withdrawn from the volume through the open proximal extremity without interference from the openwork, when the restraint is configured to be released from the appendage applied to the volume through the open proximal extremity;
    the restraint comprising:
    a channel extending through a length of the openwork between an opening through the openwork proximate to the distal extremity and a lock carried by the openwork; and
    a flexible line comprising a loop portion including an outgoing part of the flexible line extending outwardly from the channel through the opening from an end of the flexible line secured to the openwork and a standing part of the flexible line extending into the channel from the outgoing part slidably through the opening, closing the loop portion and slidably extending through the channel from the opening to the lock, wherein the lock is adjustable between an unlocked position, enabling the standing part to slide through the opening and the channel for adjusting the loop portion between a loosened appendage-receiving/releasing position and a comparatively constricted appendage-securing position, and a locked position, disabling the standing part from sliding through the opening and the channel for securing the standing part relative to the openwork for securing the loop portion.

2. The brace according to claim 1, wherein the flexible line between the opening and the lock is enclosed within the channel.

3. The brace according to claim 1, wherein the lock is proximate to the open proximal extremity.

4. A brace assembly configured to releasably secure and brace an appendage, comprising:
   a helical conduit including a proximal coil defining a proximal opening and a distal coil defining a distal opening, the helical conduit defines a volume from the proximal opening to the distal opening, extends longitudinally from the proximal coil to the distal coil, is hollow, cylindrical, and stiff, being rigid and not easily bent, and inarticulate, being jointless having no articulation or joint, and defines a helical space from the proximal coil to the distal coil defining access points to the volume between the proximal coil and the distal coil configured to enable access to an appendage between the proximal coil and the distal coil when the appendage is applied to the volume through the proximal opening; and
   a restraint carried by the helical conduit and configured to restrain the appendage from being withdrawn from the volume through the proximal opening, when the restraint is configured to be secured to the appendage applied to the volume through the proximal opening, and configured to enable the appendage for being withdrawn from the volume through the proximal opening without interference from the helical conduit, when the restraint is configured to be released from the appendage applied to the volume through the proximal opening;
   the restraint comprising:
   a channel extending through a length of the helical conduit between an opening through the helical conduit proximate to the distal coil and a lock carried by the helical conduit; and
   a flexible line comprising a loop portion including an outgoing part of the flexible line extending outwardly from the channel through the opening from an end of the flexible line secured to the helical conduit and a standing part of the flexible line extending into the channel from the outgoing part slidable through the opening, closing the loop portion and slidably extending through the channel from the opening to the lock, wherein the lock is adjustable between an unlocked position, enabling the standing part to slide through the opening and the channel for adjusting the loop portion between a loosened appendage-receiving/releasing position and a comparatively constricted appendage-securing position, and a locked position, disabling the standing part from sliding through the opening and the channel for securing the standing part relative to the helical conduit for securing the loop portion.

5. The brace according to claim 4, wherein the flexible line line between the opening and the lock is enclosed within the channel.

6. The brace according to claim 4, wherein the lock is secured to the proximal coil.

* * * * *